(12) United States Patent
Theodore et al.

(10) Patent No.: US 11,116,576 B2
(45) Date of Patent: Sep. 14, 2021

(54) DYNAMIC REFERENCE ARRAYS AND METHODS OF USE

(71) Applicant: GLOBUS MEDICAL, INC., Audubon, PA (US)

(72) Inventors: Nicholas Theodore, Paradise Valley, AZ (US); Neil R. Crawford, Chandler, AZ (US); Mitchell A. Foster, Scottsdale, AZ (US)

(73) Assignee: Globus Medical Inc., Audubon, PA (US)

( * ) Notice: Subject to any disclaimer, the term of this patent is extended or adjusted under 35 U.S.C. 154(b) by 733 days.

(21) Appl. No.: 14/602,723

(22) Filed: Jan. 22, 2015

(65) Prior Publication Data

US 2015/0209119 A1    Jul. 30, 2015

Related U.S. Application Data

(63) Continuation-in-part of application No. 13/924,505, filed on Jun. 21, 2013, now Pat. No. 9,782,229.

(Continued)

(51) Int. Cl.
*A61B 34/20* (2016.01)
*A61B 90/00* (2016.01)
(Continued)

(52) U.S. Cl.
CPC .............. *A61B 34/20* (2016.02); *A61B 90/39* (2016.02); *A61B 6/032* (2013.01); *A61B 6/12* (2013.01); *A61B 17/1757* (2013.01); *A61B 17/7047* (2013.01); *A61B 34/30* (2016.02); *A61B 90/14* (2016.02); *A61B 2034/107* (2016.02);
(Continued)

(58) Field of Classification Search
CPC ....... A61B 34/20; A61B 90/39; A61B 17/025; A61B 2090/3995; A61B 17/7047; A61B 90/14; A61B 2034/2051; A61B 2090/3966; A61B 2090/378; A61B 34/30; (Continued)

(56) References Cited

U.S. PATENT DOCUMENTS 4,150,293 A    4/1979  Franke
5,246,010 A    9/1993  Gazzara et al.
(Continued)

FOREIGN PATENT DOCUMENTS

EP    1935365 A1    6/2008
JP    2006081569    3/2006
(Continued)

OTHER PUBLICATIONS

US 8,231,638 B2, 07/2012, Swarup et al. (withdrawn)

*Primary Examiner* — Angela M Hoffa

(57) ABSTRACT

Dynamic reference arrays use markers and trackers to register a patient's anatomy to computer system. Wherein the dynamic reference array may be screwed into a patient's spinous process, clamped on to a spinous process, or attached to the spinous process using posts. In embodiments, a dynamic reference array may comprise a single structure comprising and attachment member and a scaffold. In alternate embodiments, the dynamic reference array may comprise distinct structures that allow the dynamic reference array to swivel and collapse in order to facilitate registration, while not interfering with a surgical procedure.

6 Claims, 13 Drawing Sheets

Related U.S. Application Data

(60) Provisional application No. 61/800,527, filed on Mar. 15, 2013.

(51) Int. Cl.
    *A61B 90/14*         (2016.01)
    *A61B 17/70*         (2006.01)
    *A61B 17/17*         (2006.01)
    *A61B 34/10*         (2016.01)
    *A61B 6/12*          (2006.01)
    *A61B 34/30*         (2016.01)
    *A61B 6/03*          (2006.01)

(52) U.S. Cl.
CPC .......... *A61B 2034/2051* (2016.02); *A61B 2034/2055* (2016.02); *A61B 2090/363* (2016.02); *A61B 2090/374* (2016.02); *A61B 2090/378* (2016.02); *A61B 2090/3966* (2016.02); *A61B 2090/3983* (2016.02); *A61B 2090/3991* (2016.02); *A61B 2090/3995* (2016.02)

(58) Field of Classification Search
CPC ........ A61B 2090/374; A61B 2034/107; A61B 2090/3991; A61B 2090/3983
See application file for complete search history.

(56) References Cited

U.S. PATENT DOCUMENTS

| | | | |
|---|---|---|---|
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |
| 5,825,982 | A | 10/1998 | Wright et al. |
| 5,887,121 | A | 3/1999 | Funda et al. |
| 5,911,449 | A | 6/1999 | Daniele et al. |
| 5,951,475 | A | 9/1999 | Gueziec et al. |
| 5,987,960 | A | 11/1999 | Messner et al. |
| 6,012,216 | A | 1/2000 | Esteves et al. |
| 6,031,888 | A | 2/2000 | Ivan et al. |
| 6,033,415 | A | 3/2000 | Mittelstadt et al. |
| 6,080,181 | A | 6/2000 | Jensen et al. |
| 6,106,511 | A | 8/2000 | Jensen |
| 6,122,541 | A | 9/2000 | Cosman et al. |
| 6,144,875 | A | 11/2000 | Schweikard et al. |
| 6,157,853 | A | 12/2000 | Blume et al. |
| 6,167,145 | A | 12/2000 | Foley et al. |
| 6,167,292 | A | 12/2000 | Badano et al. |
| 6,201,984 | B1 | 3/2001 | Funda et al. |
| 6,203,196 | B1 | 3/2001 | Meyer et al. |
| 6,205,411 | B1 | 3/2001 | DiGioia, III et al. |
| 6,212,419 | B1 | 4/2001 | Blume et al. |
| 6,231,565 | B1 | 5/2001 | Tovey et al. |
| 6,236,875 | B1 | 5/2001 | Bucholz et al. |
| 6,246,900 | B1 | 6/2001 | Cosman et al. |
| 6,301,495 | B1 | 10/2001 | Gueziec et al. |
| 6,306,126 | B1 | 10/2001 | Montezuma |
| 6,312,435 | B1 | 11/2001 | Wallace et al. |
| 6,314,311 | B1 | 11/2001 | Williams et al. |
| 6,320,929 | B1 | 11/2001 | Von Der Haar |
| 6,322,567 | B1 | 11/2001 | Mittelstadt et al. |
| 6,325,808 | B1 | 12/2001 | Bernard et al. |
| 6,340,363 | B1 | 1/2002 | Bolger et al. |
| 6,377,011 | B1 | 4/2002 | Ben-Ur |
| 6,379,302 | B1 | 4/2002 | Kessman et al. |
| 6,402,762 | B2 | 6/2002 | Hunter et al. |
| 6,424,885 | B1 | 7/2002 | Niemeyer et al. |
| 6,447,503 | B1 | 9/2002 | Wynne et al. |
| 6,451,027 | B1 | 9/2002 | Cooper et al. |
| 6,477,400 | B1 | 11/2002 | Barrick |
| 6,484,049 | B1 | 11/2002 | Seeley et al. |
| 6,487,267 | B1 | 11/2002 | Wolter |
| 6,490,467 | B1 | 12/2002 | Bucholz et al. |
| 6,490,475 | B1 | 12/2002 | Seeley et al. |
| 6,499,488 | B1 | 12/2002 | Hunter et al. |
| 6,501,981 | B1 | 12/2002 | Schweikard et al. |
| 6,507,751 | B2 | 1/2003 | Blume et al. |
| 6,535,756 | B1 | 3/2003 | Simon et al. |
| 6,560,354 | B1 | 5/2003 | Maurer, Jr. et al. |
| 6,565,554 | B1 | 5/2003 | Niemeyer |
| 6,587,750 | B2 | 7/2003 | Gerbi et al. |
| 6,614,453 | B1 | 9/2003 | Suri et al. |
| 6,614,871 | B1 | 9/2003 | Kobiki et al. |
| 6,619,840 | B2 | 9/2003 | Rasche et al. |
| 6,636,757 | B1 | 10/2003 | Jascob et al. |
| 6,645,196 | B1 | 11/2003 | Nixon et al. |
| 6,666,579 | B2 | 12/2003 | Jensen |
| 6,669,635 | B2 | 12/2003 | Kessman et al. |
| 6,701,173 | B2 | 3/2004 | Nowinski et al. |
| 6,719,757 | B2 * | 4/2004 | Neubauer ............ A61B 90/39 606/53 |
| 6,757,068 | B2 | 6/2004 | Foxlin |
| 6,782,287 | B2 | 8/2004 | Grzeszczuk et al. |
| 6,783,524 | B2 | 8/2004 | Anderson et al. |
| 6,786,896 | B1 | 9/2004 | Madhani et al. |
| 6,788,018 | B1 | 9/2004 | Blumenkranz |
| 6,804,581 | B2 | 10/2004 | Wang et al. |
| 6,823,207 | B1 | 11/2004 | Jensen et al. |
| 6,827,351 | B2 | 12/2004 | Graziani et al. |
| 6,837,892 | B2 | 1/2005 | Shoham |
| 6,839,612 | B2 | 1/2005 | Sanchez et al. |
| 6,856,826 | B2 | 2/2005 | Seeley et al. |
| 6,856,827 | B2 | 2/2005 | Seeley et al. |
| 6,856,828 | B2 * | 2/2005 | Cossette ............ A61B 90/39 600/429 |
| 6,879,880 | B2 | 4/2005 | Nowlin et al. |
| 6,892,090 | B2 | 5/2005 | Verard et al. |
| 6,920,347 | B2 | 7/2005 | Simon et al. |
| 6,922,632 | B2 | 7/2005 | Foxlin |
| 6,968,224 | B2 | 11/2005 | Kessman et al. |
| 6,978,166 | B2 | 12/2005 | Foley et al. |
| 6,988,009 | B2 | 1/2006 | Grimm et al. |
| 6,991,627 | B2 | 1/2006 | Madhani et al. |
| 6,996,487 | B2 | 2/2006 | Jutras et al. |
| 6,999,852 | B2 | 2/2006 | Green |
| 7,007,699 | B2 | 3/2006 | Martinelli et al. |
| 7,016,457 | B1 | 3/2006 | Senzig et al. |
| 7,043,961 | B2 | 5/2006 | Pandey et al. |
| 7,062,006 | B1 | 6/2006 | Pelc et al. |
| 7,063,705 | B2 | 6/2006 | Young et al. |
| 7,072,707 | B2 | 7/2006 | Galloway, Jr. et al. |
| 7,083,615 | B2 | 8/2006 | Peterson et al. |
| 7,097,640 | B2 | 8/2006 | Wang et al. |
| 7,099,428 | B2 | 8/2006 | Clinthorne et al. |
| 7,108,421 | B2 | 9/2006 | Gregerson et al. |
| 7,130,676 | B2 | 10/2006 | Barrick |
| 7,139,418 | B2 | 11/2006 | Abovitz et al. |
| 7,139,601 | B2 | 11/2006 | Bucholz et al. |
| 7,155,316 | B2 | 12/2006 | Sutherland et al. |
| 7,164,968 | B2 | 1/2007 | Treat et al. |
| 7,167,738 | B2 | 1/2007 | Schweikard et al. |
| 7,169,141 | B2 | 1/2007 | Brock et al. |
| 7,172,627 | B2 | 2/2007 | Fiere et al. |
| 7,194,120 | B2 | 3/2007 | Wicker et al. |
| 7,197,107 | B2 | 3/2007 | Arai et al. |
| 7,231,014 | B2 | 6/2007 | Levy |
| 7,231,063 | B2 | 6/2007 | Naimark et al. |
| 7,239,940 | B2 | 7/2007 | Wang et al. |
| 7,248,914 | B2 | 7/2007 | Hastings et al. |
| 7,301,648 | B2 | 11/2007 | Foxlin |
| 7,302,288 | B1 | 11/2007 | Schellenberg |
| 7,313,430 | B2 | 12/2007 | Urquhart et al. |
| 7,318,805 | B2 | 1/2008 | Schweikard et al. |
| 7,318,827 | B2 | 1/2008 | Leitner et al. |
| 7,319,897 | B2 | 1/2008 | Leitner et al. |
| 7,324,623 | B2 | 1/2008 | Heuscher et al. |
| 7,327,865 | B2 | 2/2008 | Fu et al. |
| 7,331,967 | B2 | 2/2008 | Lee et al. |
| 7,333,642 | B2 | 2/2008 | Green |
| 7,339,341 | B2 | 3/2008 | Oleynikov et al. |

(56) References Cited

U.S. PATENT DOCUMENTS

| | | | |
|---|---|---|---|
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,643,867 B2 * | 1/2010 | Solar .................. A61B 90/39 356/247 |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,862,568 B2 * | 1/2011 | Vilsmeier .............. A61B 17/86 606/86 R |
| 7,862,570 B2 * | 1/2011 | Russell ................ A61B 90/50 600/424 |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,032,204 B2 * | 10/2011 | Solar .................. A61B 90/39 378/20 |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,185,184 B2 * | 5/2012 | Solar .................. A61B 90/39 600/407 |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |

(56) References Cited

U.S. PATENT DOCUMENTS

| | | |
|---|---|---|
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,357,165 B2 * | 1/2013 | Grant ............... A61B 90/36 606/86 R |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,491,597 B2 * | 7/2013 | Russell ............... A61B 90/50 606/130 |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |

(56) References Cited

U.S. PATENT DOCUMENTS

| | | | |
|---|---|---|---|
| 8,894,688 B2 | 11/2014 | Suh | |
| 8,894,691 B2 | 11/2014 | Iott et al. | |
| 8,906,069 B2 | 12/2014 | Hansell et al. | |
| 8,964,934 B2 | 2/2015 | Ein-Gal | |
| 8,992,580 B2 | 3/2015 | Bar et al. | |
| 8,996,169 B2 | 3/2015 | Lightcap et al. | |
| 9,001,963 B2 | 4/2015 | Sowards-Emmerd et al. | |
| 9,002,076 B2 | 4/2015 | Khadem et al. | |
| 9,044,190 B2 | 6/2015 | Rubner et al. | |
| 9,084,635 B2 * | 7/2015 | Nuckley | A61B 17/7047 |
| 9,107,683 B2 | 8/2015 | Hourtash et al. | |
| 9,125,556 B2 | 9/2015 | Zehavi et al. | |
| 9,131,986 B2 | 9/2015 | Greer et al. | |
| 9,215,968 B2 | 12/2015 | Schostek et al. | |
| 9,308,050 B2 | 4/2016 | Kostrzewski et al. | |
| 9,380,984 B2 | 7/2016 | Li et al. | |
| 9,393,039 B2 | 7/2016 | Lechner et al. | |
| 9,398,886 B2 | 7/2016 | Gregerson et al. | |
| 9,398,890 B2 | 7/2016 | Dong et al. | |
| 9,414,859 B2 | 8/2016 | Ballard et al. | |
| 9,420,975 B2 | 8/2016 | Gutfleisch et al. | |
| 9,492,235 B2 | 11/2016 | Hourtash et al. | |
| 9,498,290 B2 * | 11/2016 | Piferi | A61N 1/0534 |
| 9,592,096 B2 | 3/2017 | Maillet et al. | |
| 9,737,370 B2 * | 8/2017 | Kheradpir | A61B 34/20 |
| 9,750,465 B2 | 9/2017 | Engel et al. | |
| 9,757,203 B2 | 9/2017 | Hourtash et al. | |
| 9,795,354 B2 | 10/2017 | Menegaz et al. | |
| 9,814,535 B2 | 11/2017 | Bar et al. | |
| 9,820,783 B2 | 11/2017 | Donner et al. | |
| 9,833,265 B2 | 11/2017 | Donner et al. | |
| 9,848,922 B2 | 12/2017 | Tohmeh et al. | |
| 9,925,011 B2 | 3/2018 | Gombert et al. | |
| 9,931,025 B1 | 4/2018 | Graetzel et al. | |
| 10,034,717 B2 | 7/2018 | Miller et al. | |
| 2001/0036302 A1 | 11/2001 | Miller | |
| 2002/0035321 A1 | 3/2002 | Bucholz et al. | |
| 2002/0107518 A1 * | 8/2002 | Neubauer | A61B 90/39 606/54 |
| 2003/0078565 A1 * | 4/2003 | Vilsmeier | A61B 17/86 606/1 |
| 2004/0030237 A1 | 2/2004 | Lee et al. | |
| 2004/0068172 A1 | 4/2004 | Nowinski et al. | |
| 2004/0076259 A1 | 4/2004 | Jensen et al. | |
| 2004/0167391 A1 * | 8/2004 | Solar | A61B 90/39 600/411 |
| 2004/0167393 A1 | 8/2004 | Solar et al. | |
| 2005/0096502 A1 | 5/2005 | Khalili | |
| 2005/0143651 A1 | 6/2005 | Verard et al. | |
| 2005/0171558 A1 | 8/2005 | Abovitz et al. | |
| 2005/0215888 A1 | 9/2005 | Grimm et al. | |
| 2005/0267358 A1 | 12/2005 | Tuma et al. | |
| 2006/0052792 A1 | 3/2006 | Boettiger et al. | |
| 2006/0100610 A1 | 5/2006 | Wallace et al. | |
| 2006/0173329 A1 | 8/2006 | Marquart et al. | |
| 2006/0184396 A1 | 8/2006 | Dennis et al. | |
| 2006/0241416 A1 | 10/2006 | Marquart et al. | |
| 2006/0291612 A1 | 12/2006 | Nishide et al. | |
| 2007/0015987 A1 | 1/2007 | Benlloch Baviera et al. | |
| 2007/0021738 A1 | 1/2007 | Hasser et al. | |
| 2007/0038059 A1 | 2/2007 | Sheffer et al. | |
| 2007/0073133 A1 | 3/2007 | Schoenefeld | |
| 2007/0156121 A1 | 7/2007 | Millman et al. | |
| 2007/0156157 A1 | 7/2007 | Nahum et al. | |
| 2007/0160439 A1 * | 7/2007 | Vilsmeier | A61B 17/86 411/378 |
| 2007/0167712 A1 | 7/2007 | Keglovich et al. | |
| 2007/0225599 A1 * | 9/2007 | Solar | A61B 90/39 600/426 |
| 2007/0233238 A1 | 10/2007 | Huynh et al. | |
| 2008/0004523 A1 | 1/2008 | Jensen | |
| 2008/0013809 A1 | 1/2008 | Zhu et al. | |
| 2008/0033283 A1 | 2/2008 | Dellaca et al. | |
| 2008/0046122 A1 | 2/2008 | Manzo et al. | |
| 2008/0082109 A1 | 4/2008 | Moll et al. | |
| 2008/0108912 A1 | 5/2008 | Node-Langlois | |
| 2008/0108991 A1 | 5/2008 | Von Jako | |
| 2008/0109012 A1 | 5/2008 | Falco et al. | |
| 2008/0144906 A1 | 6/2008 | Allred et al. | |
| 2008/0161680 A1 | 7/2008 | Von Jako et al. | |
| 2008/0161682 A1 | 7/2008 | Kendrick et al. | |
| 2008/0177173 A1 * | 7/2008 | Deffenbaugh | A61B 90/36 600/414 |
| 2008/0177203 A1 | 7/2008 | von Jako | |
| 2008/0214922 A1 | 9/2008 | Hartmann et al. | |
| 2008/0228068 A1 | 9/2008 | Viswanathan et al. | |
| 2008/0228196 A1 | 9/2008 | Wang et al. | |
| 2008/0235052 A1 | 9/2008 | Node-Langlois et al. | |
| 2008/0269596 A1 | 10/2008 | Revie et al. | |
| 2008/0287771 A1 | 11/2008 | Anderson | |
| 2008/0287781 A1 | 11/2008 | Revie et al. | |
| 2008/0300477 A1 | 12/2008 | Lloyd et al. | |
| 2008/0300478 A1 | 12/2008 | Zuhars et al. | |
| 2008/0302950 A1 | 12/2008 | Park et al. | |
| 2008/0306490 A1 | 12/2008 | Lakin et al. | |
| 2008/0319311 A1 | 12/2008 | Hamadeh | |
| 2009/0012509 A1 | 1/2009 | Csavoy et al. | |
| 2009/0030428 A1 | 1/2009 | Omori et al. | |
| 2009/0080737 A1 | 3/2009 | Battle et al. | |
| 2009/0185655 A1 | 7/2009 | Koken et al. | |
| 2009/0198121 A1 | 8/2009 | Hoheisel | |
| 2009/0216113 A1 | 8/2009 | Meier et al. | |
| 2009/0228019 A1 | 9/2009 | Gross et al. | |
| 2009/0259123 A1 | 10/2009 | Navab et al. | |
| 2009/0259230 A1 | 10/2009 | Khadem et al. | |
| 2009/0264899 A1 | 10/2009 | Appenrodt et al. | |
| 2009/0281417 A1 | 11/2009 | Hartmann et al. | |
| 2009/0306499 A1 | 12/2009 | Van Vorhis et al. | |
| 2010/0022874 A1 | 1/2010 | Wang et al. | |
| 2010/0039506 A1 | 2/2010 | Sarvestani et al. | |
| 2010/0063388 A1 * | 3/2010 | Solar | A61B 90/39 600/426 |
| 2010/0125286 A1 | 5/2010 | Wang et al. | |
| 2010/0130986 A1 | 5/2010 | Mailloux et al. | |
| 2010/0228117 A1 | 9/2010 | Hartmann | |
| 2010/0228265 A1 | 9/2010 | Prisco | |
| 2010/0249571 A1 | 9/2010 | Jensen et al. | |
| 2010/0274120 A1 | 10/2010 | Heuscher | |
| 2010/0280363 A1 | 11/2010 | Skarda et al. | |
| 2010/0331858 A1 | 12/2010 | Simaan et al. | |
| 2011/0022229 A1 | 1/2011 | Jang et al. | |
| 2011/0077504 A1 | 3/2011 | Fischer et al. | |
| 2011/0098553 A1 | 4/2011 | Robbins et al. | |
| 2011/0118750 A1 | 5/2011 | Wu et al. | |
| 2011/0137152 A1 | 6/2011 | Li | |
| 2011/0213384 A1 | 9/2011 | Jeong | |
| 2011/0224684 A1 | 9/2011 | Larkin et al. | |
| 2011/0224685 A1 | 9/2011 | Larkin et al. | |
| 2011/0224686 A1 | 9/2011 | Larkin et al. | |
| 2011/0224687 A1 | 9/2011 | Larkin et al. | |
| 2011/0224688 A1 | 9/2011 | Larkin et al. | |
| 2011/0224689 A1 | 9/2011 | Larkin et al. | |
| 2011/0224825 A1 | 9/2011 | Larkin et al. | |
| 2011/0230967 A1 | 9/2011 | O'Halloran et al. | |
| 2011/0238080 A1 | 9/2011 | Ranjit et al. | |
| 2011/0276058 A1 | 11/2011 | Choi et al. | |
| 2011/0282189 A1 | 11/2011 | Graumann | |
| 2011/0286573 A1 | 11/2011 | Schretter et al. | |
| 2011/0295062 A1 | 12/2011 | Gratacos Solsona et al. | |
| 2011/0295370 A1 | 12/2011 | Suh et al. | |
| 2011/0306986 A1 | 12/2011 | Lee et al. | |
| 2012/0035507 A1 | 2/2012 | George et al. | |
| 2012/0046668 A1 | 2/2012 | Gantes | |
| 2012/0051498 A1 | 3/2012 | Koishi | |
| 2012/0053597 A1 | 3/2012 | Anvari et al. | |
| 2012/0059248 A1 | 3/2012 | Holsing et al. | |
| 2012/0071753 A1 | 3/2012 | Hunter et al. | |
| 2012/0108954 A1 | 5/2012 | Schulhauser et al. | |
| 2012/0123299 A1 | 5/2012 | Neubauer et al. | |
| 2012/0136372 A1 | 5/2012 | Amat Girbau et al. | |
| 2012/0143084 A1 | 6/2012 | Shoham | |
| 2012/0184839 A1 | 7/2012 | Woerlein | |
| 2012/0197182 A1 | 8/2012 | Millman et al. | |

(56) References Cited

U.S. PATENT DOCUMENTS

| | | |
|---|---|---|
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0090692 A1* | 4/2013 | Nuckley ............ A61B 17/7047 606/277 |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345718 A1* | 12/2013 | Crawford ............ A61B 17/025 606/130 |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Rah et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0031982 A1* | 1/2015 | Piferi ............ A61N 1/0534 600/411 |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0182293 A1* | 7/2015 | Yang ............ A61B 5/064 600/424 |
| 2015/0196261 A1 | 7/2015 | Funk |
| 2015/0213633 A1 | 7/2015 | Chang et al. |
| 2015/0282735 A1* | 10/2015 | Rossner ............ A61B 90/39 600/424 |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0220145 A1* | 8/2016 | Rossner ............ A61B 90/39 |
| 2016/0228033 A1* | 8/2016 | Rossner ............ A61B 90/39 |
| 2016/0235480 A1 | 8/2016 | Scholl et al. |
| 2016/0242849 A9* | 8/2016 | Crawford ............ A61B 17/025 |
| 2016/0249990 A1 | 9/2016 | Glozman et al. |
| 2016/0256225 A1* | 9/2016 | Crawford ............ A61B 34/20 |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2016/0354153 A1* | 12/2016 | Hodgson ............ A61B 90/39 |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0252109 A1* | 9/2017 | Yang ............ A61B 5/064 |
| 2017/0258426 A1 | 9/2017 | Risher-Kelly et al. |
| 2017/0258535 A1* | 9/2017 | Crawford ............ A61B 34/32 |
| 2017/0273748 A1 | 9/2017 | Hourtash et al. |

(56) References Cited

U.S. PATENT DOCUMENTS

2017/0296277 A1  10/2017  Hourtash et al.
2017/0360493 A1  12/2017  Zucher et al.

FOREIGN PATENT DOCUMENTS

| JP | 2006518655 | | 8/2006 |
| WO | 2006030637 | A1 | 3/2006 |
| WO | 2014005225 | A1 | 1/2014 |

* cited by examiner

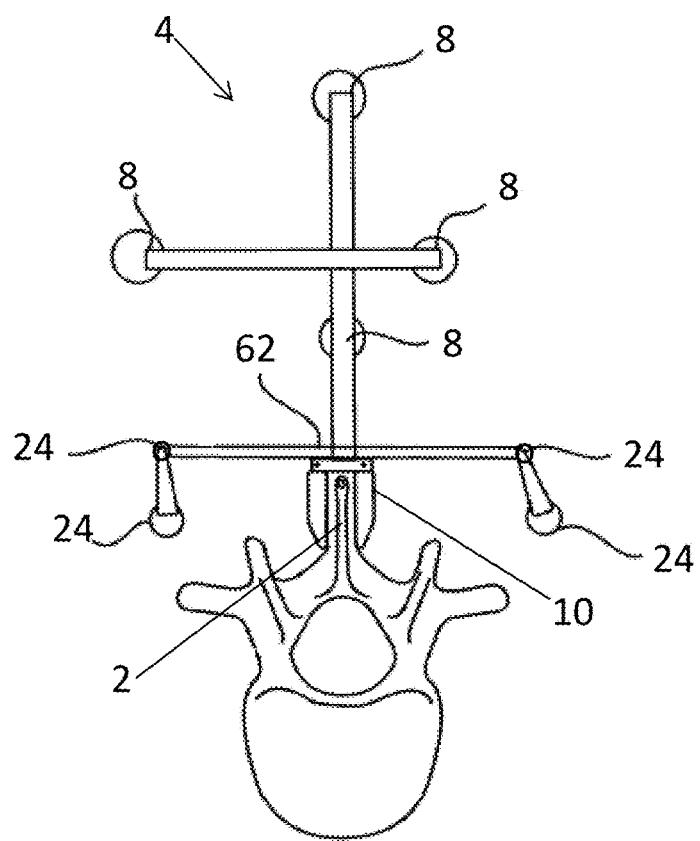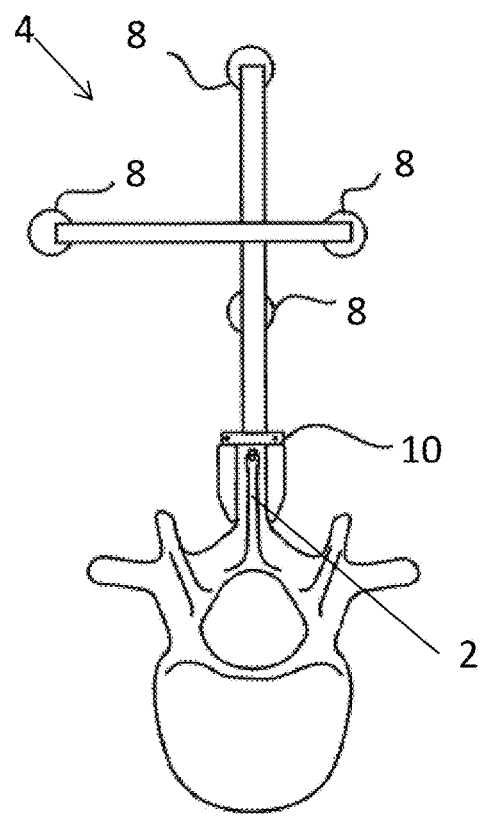
FIG. 8A   FIG. 8B

DYNAMIC REFERENCE ARRAYS AND METHODS OF USE

CROSS-REFERENCE TO RELATED APPLICATIONS

This application is a continuation-in-part of U.S. application Ser. No. 13/924,505, entitled "Surgical Robot Platform," filed on Jun. 21, 2013, which is a non-provisional of U.S. application Ser. No. 61/800,527 filed on Mar. 15, 2013, which is a provisional claiming priority to U.S. Provisional Patent Application No. 61/662,702 filed on Jun. 21, 2012, which are incorporated herein by reference in their entirety.

BACKGROUND

Embodiments are directed to surgical navigation procedures and, more particularly, embodiments are directed to dynamic reference arrays, which include a plurality of active members, where the active members may be radio-opaque fiducial markers and tracking markers.

Dynamic reference arrays may typically be rigid bodies that may be temporarily attached to a patient's anatomy during a navigated surgical procedures. Dynamic reference arrays may also commonly be referred to as "targeting fixtures." Dynamic reference arrays may comprise marker trees, which may be attached to the patient's anatomy using pins or clamps to the bone. A dynamic reference array's purpose is to allow real-time tracking of the 3D position of the patient's anatomy and mapping a patient's anatomy to a computerized three-dimensional (3D) coordinate system. When a dynamic reference array is registered, it is possible for a mechanical system such as a robot to target a location on the patient's anatomy corresponding to a known location in the computerized 3D coordinate system, enabling the mechanical system to guide insertion of a screw or needle, or perform another surgical or therapeutic procedure requiring targeting. Registering dynamic reference arrays may be done using point-to-point registration, point cloud registration, or alternative methods.

Point-to-point registration requires common, known points in the camera coordinate system and the anatomical coordinate system to be identified. The anatomical landmarks or reference marks on a feature of the dynamic reference arrays may be identified using a digitizing probe, which may be a wand with embedded tracking markers that enable the system to extrapolate the 3D location of the wand's tip based on positions of the fiducial markers embedded in the wand's handle. As an example, an image guidance system may indicate to the user through a software feature that the tip of the spinous process of L4 should now be touched by the wand, and the user may physically touch that point with the tool while confirming this procedure on software. Then the system may indicate that the tip of the spinous process of L5 should be touched by the wand, then other points, with the process repeated until enough points are identified to ensure good co-registration of the anatomical and camera coordinate systems.

Point cloud registration may typically require an array (cloud) of points to be identified manually by the user, typically by dragging the tip of a digitizing probe or wand across the surface of bone. After the bony contours may be characterized, the system may search the anatomical image for a matching bone surface contour. If the contour of the physically identified point array matches a contour found through image processing of the bony anatomy, then the anatomical coordinate system and the camera coordinate system may then be co-registered accurately. The methods of point-to-point registration and point cloud registration are known in the art.

In addition to using the methods of point-to-point registration and point cloud registration, an alternative method of automatic registration may be used that makes use of an additional piece that is temporarily or permanently mounted on the dynamic reference arrays. This registration method may automatically or manually locate in software the positions in the 3D medical image volume of three or more radio-opaque fiducial markers, referred to as a "fiducial array". Radio-opaque refers to the property that the fiducial markers are visible and distinguishable in the 3D volume of the medical image. The physical positions of these fiducial markers may be found from the optical tracking system without user intervention because the fiducial markers may be mounted to a dynamic reference array in a known position relative to the tracking markers that are part of the dynamic reference array. Using this fixed relationship of fiducial to tracking markers, the known positions of the fiducial markers in the 3D image volume, and the detected positions of the tracking markers in the camera coordinate system, co-registration of the camera and image coordinate systems is possible.

It is preferable to mount the fiducial array near the location on the patient at which surgery is to be performed because the accuracy of localizing the anatomy decreases with increasing distance from the fiducials. However, it is preferable to mount the tracking markers away from the location on the patient at which surgery is to be performed so that the tracking markers do not interfere with positioning of surgical tools, retractors, etc.

Consequently, there is a need for a device that may use both radio-opaque fiducials and tracking members on the same dynamic reference array. Further, there is a need for positioning the dynamic reference array as close as possible the patient's anatomy, while not interfering with surgical tools during a surgery. The ability to perform operations on a patient with a single dynamic reference array greatly diminish the time consumed in preparation for surgery and during surgery. The application of the dynamic reference array and the techniques used with the dynamic reference array may enhance the overall surgical operation and the results of the operation.

SUMMARY

These and other needs in the art are addressed in one embodiment wherein a dynamic reference array may comprise a scaffold, a plurality of markers coupled to the scaffold, and an attachment member coupled to the scaffold with a swivel feature, wherein the attachment member is configured to secure the dynamic reference array to a patient while allowing movement of the scaffold with respect to the attachment member. In other embodiments, a method is addressed using a dynamic reference array that may comprise attaching the dynamic reference array to a patient, scanning the patient while a scaffold on the dynamic reference array is in a first position, registering the dynamic reference array to the patient's anatomy, and moving the scaffold into a second position while the dynamic reference array remains attached to the patient.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which:

FIG. 8A illustrates a clamping mechanism modified with a dynamic reference array including a temporary marker skirt;

FIG. 8B illustrates a clamping mechanism modified with a dynamic reference array with the temporary marker skirt detached;

DETAILED DESCRIPTION

Dynamic reference arrays, herein referred to as "DRAs", are rigid bodies that are temporarily attached to the patient during a navigated surgical procedure. Their purpose may be to allow 3D localization systems to track the positions of tracking markers that are embedded in the DRA, and thereby track the real-time position of relevant anatomy. A step that may be needed before such tracking may provide useful data may be to register the anatomy such that the transformation from the coordinate system of the anatomy (for example, a 3D CT scan volume) to the coordinate system of the tracking system may be defined. Registration methods are briefly discussed below.

Figure 1:
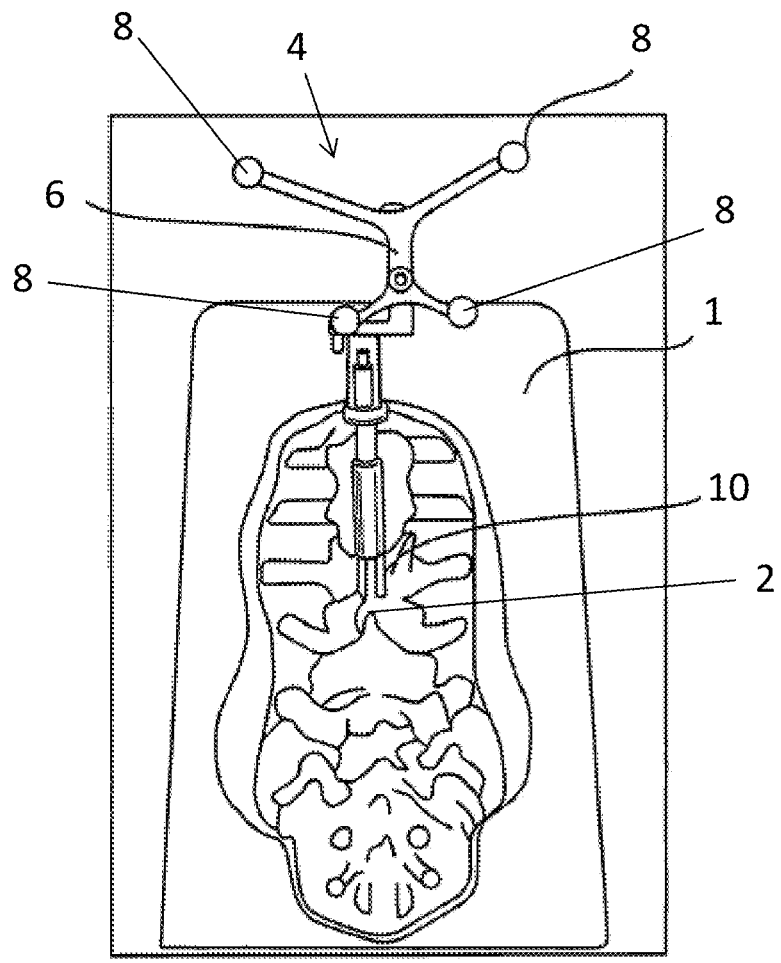
FIG. 1 illustrates an embodiment of a dynamic tracking device mounted to the spinous process of the lumbar spine of a human spine model.

FIG. 1 illustrates a representation of a spinous process 2 within a model of a patient 1. A DRA 4 may be attached to spinous process 2. This particular DRA 4 comprises a scaffold 6, a plurality of tracking markers 8 and a clamp mechanism 10. Scaffold 6 and clamp mechanism 10 may be in a single structure or connected by an angular adjustment swivel feature 12, as illustrated in FIGS. 9A, 9B, 10A, and 10B. Swivel feature 12 may include a hinge, ball-and-socket or other suitable joint to allow the orientation of scaffold 6 to be adjusted while DRA 4 remains rigidly clamped or fastened to bone. Tracking markers 8 may be positioned at any suitable location on scaffold 6. Tracking markers 8 may be any lightweight device whose 3D position may be sensed accurately using a detector. For example, tracking markers 8 may be reflective spheres tracked using stereophotogrammetry by two or more optical cameras, infrared-emitting diodes tracked using stereophotogrammetry by two or more optical cameras, magnetic sensors capable of detecting the position within a magnetic field, and/or radiofrequency emitters whose position may be sensed through time-of-flight to radiofrequency receivers in fixed known positions around the room. The positions of tracking markers 8 relative to their tracking system may be adjusted using swivel feature 12. For example, the positions of reflective spheres on DRA 4 may be adjusted using swivel feature 12 so that there may be better line of sight from the cameras to the fixture.

Figure 2:
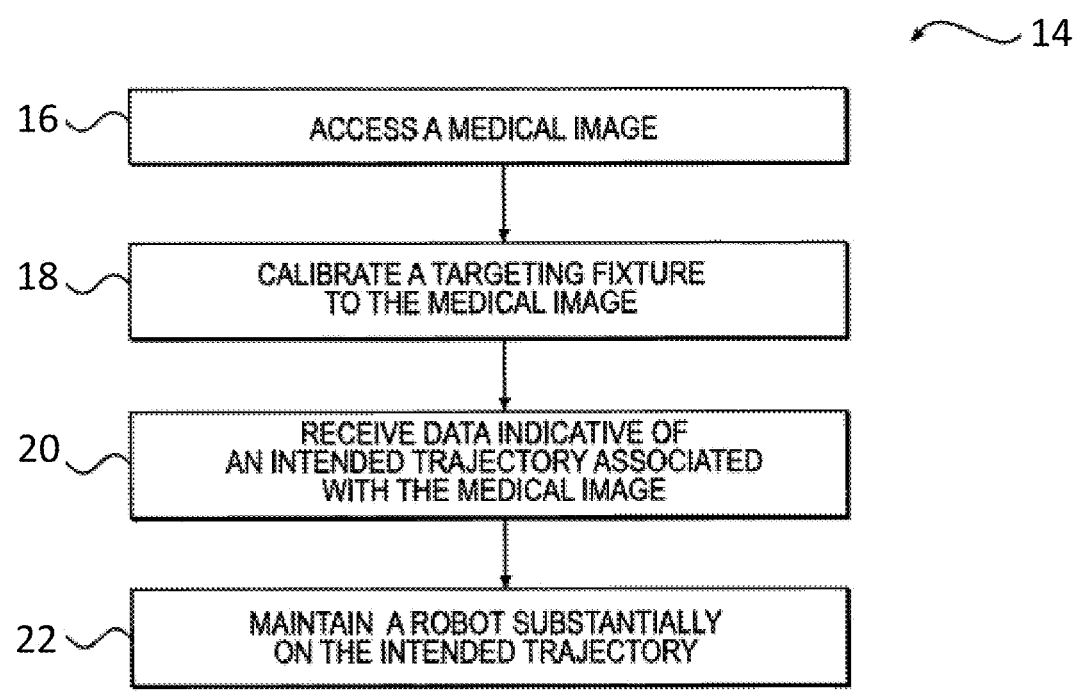
FIG. 2 illustrates an embodiment of methods for registering (calibrating) and tracking.

FIG. 2 illustrates an algorithm, which may be used in a registration method. As illustrated, a registration method 14 begins with block 16. Block 16 may comprise accessing (e.g., receiving, retrieving, or otherwise acquiring) a medical image. As described herein, the medical image may be a 3D anatomical image scan including, but not limited to a CT scan, a magnetic resonance imaging scan (hereinafter referred to as an "MRI scan"), three-dimensional fluoroscopy scan, and/or other anatomical scan. It should be appreciated that any 3D anatomical scan may be utilized with a surgical robot, not illustrated, and may be within the scope of the present invention. In some embodiments, at block 18, registration method 14 may further comprise calibrating a DRA 4 to the medical image. In some embodiments, the calibration may be semi-automated or automated. In some embodiments, at block 20, the registration method 14 may further comprise receiving data indicative of an intended trajectory associated with the medical image. In some embodiments, at block 22, after registration is complete, registration method 14 may further comprise maintaining a robot substantially on the intended trajectory. In some embodiments, a control platform (not illustrated) may adjust movement of the robot in order to substantially maintain the intended trajectory.

Figure 3:
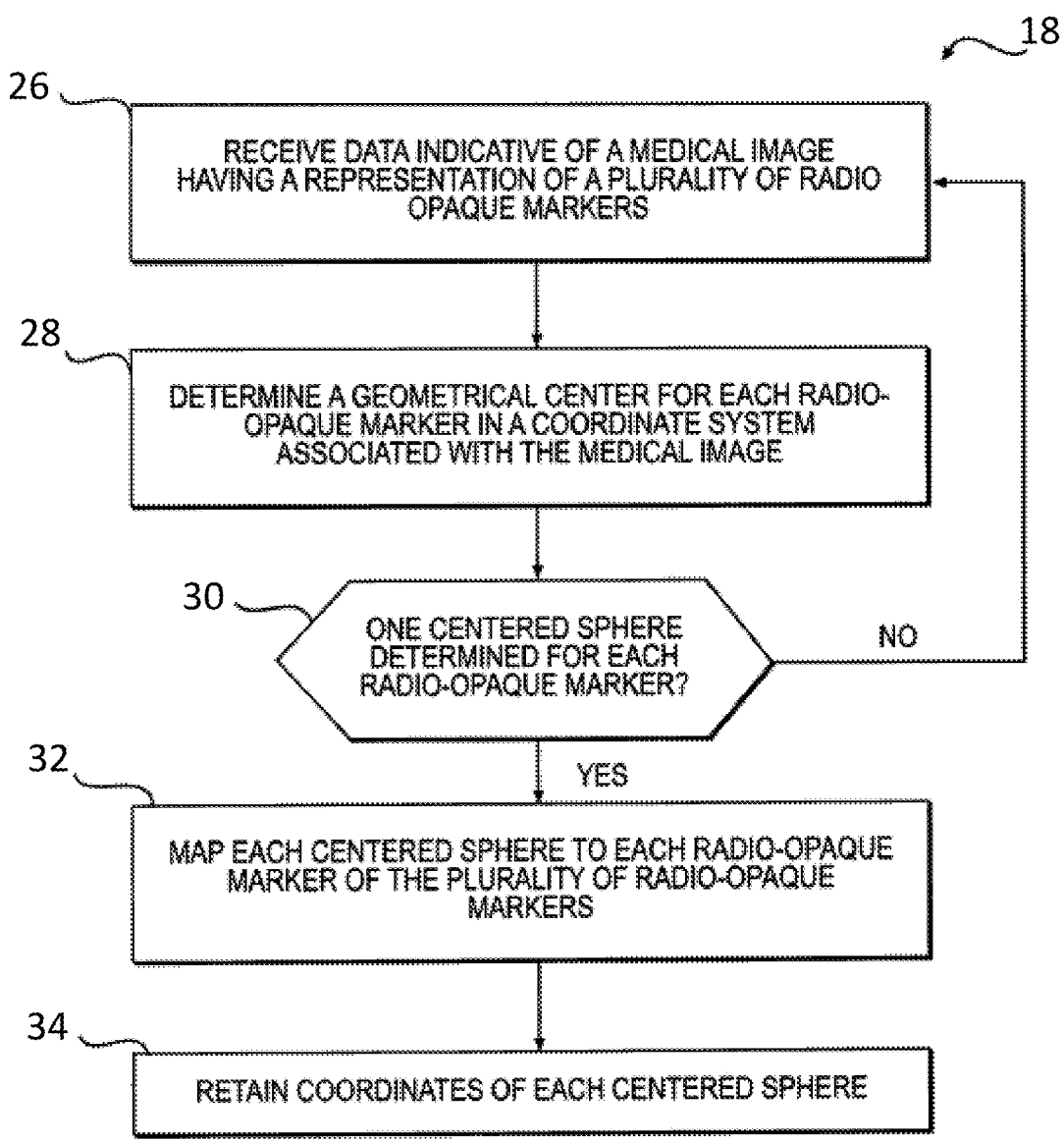
FIG. 3 illustrates an embodiment of methods for registration of a medical image using detected coordinates of radio-opaque fiducial markers.

As illustrated in FIG. 3, block 18, to register a DRA 4 to the medical image a semi-automated calibration method may be implemented. Starting with block 26, data indicative of a medical image having a representation of a plurality of radio-opaque fiducial markers 24 (e.g., tracking markers 8 on FIG. 1) may be received. In one embodiment, as described herein, such plurality may contain four fiducial markers 24. In some embodiments, at block 28, a geometrical center for each fiducial marker 24 may be determined in a coordinate system associated with the medical image.

In some embodiments, image thresholding may be utilized to define one or more edges of each fiducial marker 24 and a geometrical center thereof. Thresholding refers to an image processing technique in which pixel intensity within a two dimensional (2D) region may be monitored. For example, the x, y positions (for instance expressed in mm) of pixels of an intensity that reach a predetermined value may be retrieved. Stated similarly, the threshold refers to the transition pixel intensity from light to dark. In some embodiments, on 2D slices of the medical image, fiducial marker 24 may appear light and the adjacent space (such as tissue or air) may appear dark. In some embodiments, displaying pixels that satisfy a thresholding criterion at an intensity encountered at the edge of a fiducial marker 24 may yield a largely circular trace outlining the marker on the medical image. Since in some embodiments, fiducial markers 24 may be spherical, a method for finding the center of fiducial marker 24 in a 2D view may include firstly restricting the 2D view to a sampling region with the high-intensity image of the sphere toward the center of the region and pixels of lower intensity toward the outer edges of the region. Secondly, the method may include finding the mean x threshold position (e.g., the maximum x coordinate of pixels satisfying the threshold criterion plus minimum x coordinate of pixels satisfying the threshold criterion divided by two), and finding the mean y threshold position using a similar method.

In some embodiments, the center of the sphere may be found by determining 2D centers of slices through the same fiducial marker 24 in two orthogonal views. For example, in some embodiments, the method may include finding mean x and mean y from an xy slice, then finding mean x and mean z from an xz slice to get a mean x, y, and z axis coordinate representing the center of fiducial marker 24. Further, upon or after the mean x, mean y, and mean z are found, new xy and xz slices may be evaluated again and the maximum and minimum x, y, and z threshold values may be again determined to evaluate the dimensions of the thresholded object in each view. It may be appreciated from this method that in some embodiments, a non-spherical object of high intensity, such as a small process of cortical bone extending away from the side of the spine, may fail to satisfy (1) a condition where there may be high intensity near the middle of the region, but low intensity all around, since the process may extend out of the region in one or more directions; or (2) a condition where the dimensions in x, y, and z of the centered object do not match each other (e.g., non-spherical case).

As illustrated in FIG. 3, in some embodiments, at block 30, it is ascertained if one centered sphere is determined for each fiducial marker 24 for the fixture being calibrated. In some embodiments, when at least one such sphere is not determined, or identified, the threshold setting is adjusted and flow is directed to block 26. In some embodiments, at block 32, each centered sphere is mapped to each fiducial marker 24 of the plurality of fiducial markers 24. As illustrated, in some embodiments, block 32 may represent a mapping action which, in some embodiments, may comprise implementing a sorting process to establish a specific centered sphere is associated with a specific one of the plurality of fiducial markers 24.

In some embodiments, a plurality of fiducial markers 24 may contain four fiducial markers 24 (represented, for example, as OP1, OP2, OP3, and OP4). In some embodiments, the sorting process may map each one of four centered fiducial markers 24 to one of OP1, OP2, OP3, or OP4. In some embodiments, the sorting process may distinguish a specific fiducial marker 24 by measuring inter-marker distances from mean positions of the four unidentified fiducial markers 24, and comparing such distances to extant inter-marker distances (for example, those that are pre-measured and retained in memory, such as mass storage device) for each fiducial marker 24 on a marker fixture. In some embodiments, fiducial markers 24 on DRA 4 may be placed asymmetrically, each fiducial marker 24 may be identified from a unique set of inter-marker distances corresponding to such fiducial marker 24. For example, in some embodiments where the sum of inter-marker distances of one unknown fiducial marker 24 relative to the other threes fiducial markers 24 measured from the medical image is D, a single physical fiducial marker 24 (one of OP1, OP2, OP3, or OP4) may have a matching inter-marker distance sum within a specified tolerance (such as ±1 mm) of D. In some embodiments, at block 34, coordinates of each centered sphere may be retained (for example in memory of a computer platform).

FIGS. 4A-4E illustrate alternate guidance systems used with a surgical robot system. In embodiments, a surgical robot system, not illustrated, may comprise a DRA 4 for use with a guidance system. In some embodiments, one DRA 4 comprises a calibration frame 36, as illustrated in FIGS. 4A-4E. A calibration frame 36 may be used in connection with many invasive procedures. For example, calibration frame 36 may be used in thoracolumbar pedicle screw insertion in order to help achieve a more accurate trajectory position. In some embodiments, the use of calibration frame 36 may simplify the calibration procedure. In some embodiments of the invention, calibration frame 36 may be temporarily affixed to the skin of a patient 1 (e.g., FIG. 1) surrounding a selected site for a medical procedure, and then the medical procedure may be performed through a window defined by calibration frame 36.

Figure 4A:
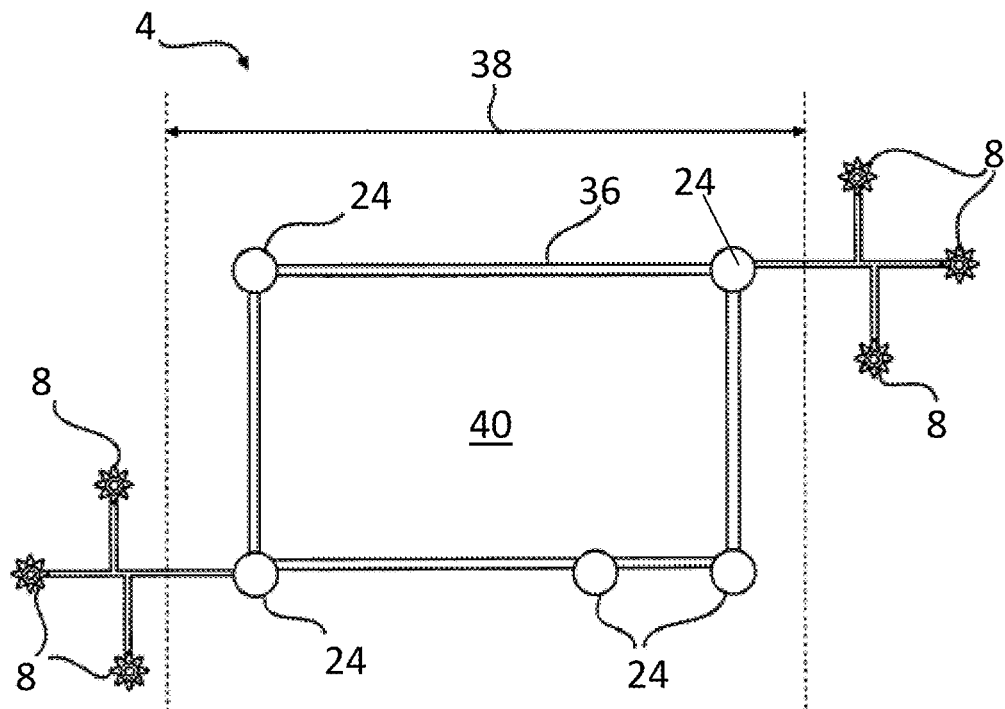
FIG. 4A illustrates an embodiment of the use of calibration frames with the guidance system.
Figure 4B:
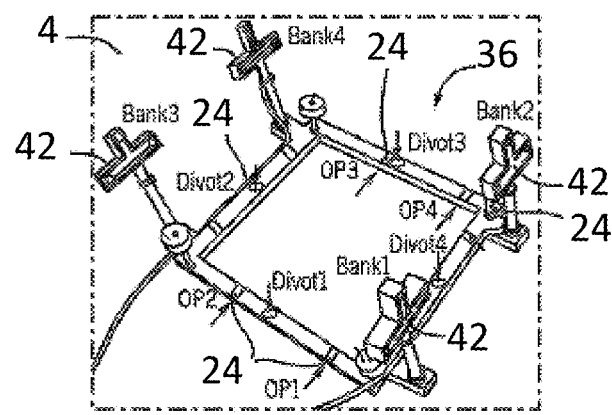
FIG. 4B illustrates an embodiment of the use of calibration frames with the guidance system.
Figure 4C:
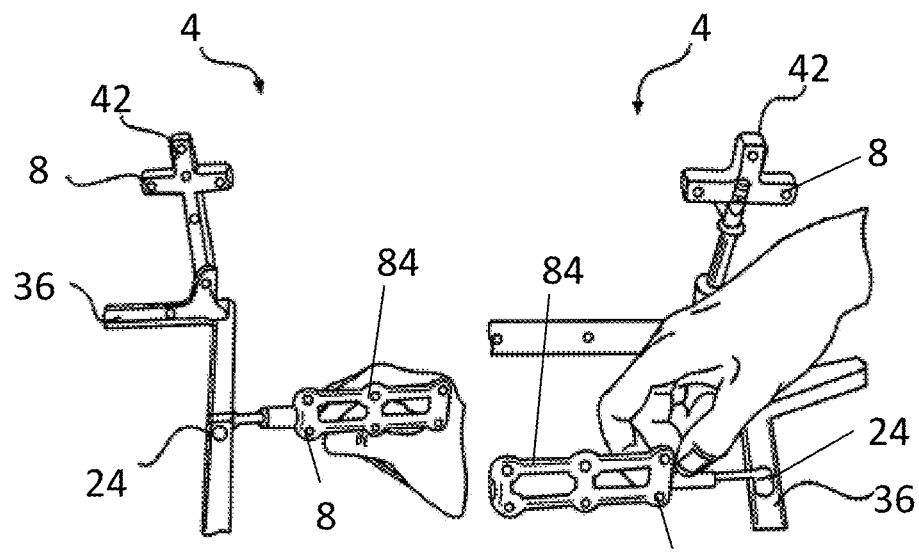
FIG. 4C illustrates an embodiment of the characterization of calibration frames with the guidance system.

As illustrated in FIGS. 4A and 4B, in some embodiments of the invention, calibration frame 36 may comprise a combination of fiducial markers 24 and tracking markers 8. In some embodiments, fiducial markers 24 may be located within CT scan region 38, and tracking markers 8 may be located outside of CT scan region 38. In some embodiments, a surgical field 40 (i.e., the area where the invasive procedure will occur) may be located within the perimeter created by fiducial markers 24. In some embodiments, the actual distances of fiducial markers 24 and tracking markers 8 relative to each other may be measured from a high-precision laser scan of calibration frame 36. Additionally or alternatively, in some embodiments, the actual relative distances may be measured by actively measuring the positions of tracking markers 8 while nearly simultaneously or simultaneously pointing with a pointing device, such as a conventional digitizing probe, to one or more locations on the surface of the fiducial markers 24. In certain embodiments, digitizing probes 84 may comprise tracking markers 8 embedded in a rigid body and a tip extending from rigid body.

Figure 4D:
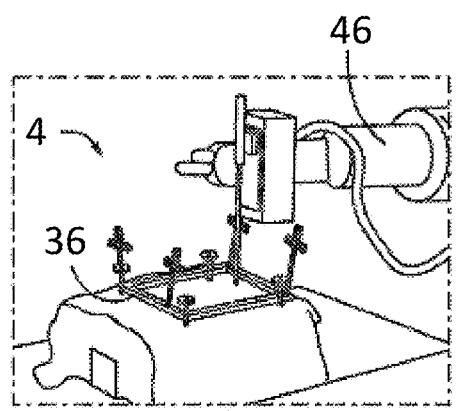
FIG. 4D illustrates an embodiment of the use of calibration frames with the guidance system.

In some applications, to establish the spatial relationship between tracking markers 8 and fiducial markers 24, a conventional digitizing probe, such as a 6-marker probe 84, embedded with tracking markers 8 in a known relationship to the probe's tip (see for example FIG. 4C) may be used to point to each fiducial markers 24. In some embodiments, the probe 84 may point to locations on two opposite surfaces of spherical fiducial markers 24 while recording the position of the probe tip and tracking markers 8 on calibration frame 36 simultaneously. Then, the average position of the two surface coordinates may be taken, corresponding to the center of the sphere. An image of a robot 46, which may be used with DRA 4 is illustrated in FIG. 4D. For placement of conventional surgical screws, a biopsy, injection, or other procedures, in some embodiments, robot 46 may work through the window formed by calibration frame 36. During a surgical procedure, in some embodiments, the working portal is kept on the interior of calibration frame 36 and fiducial markers 24 on the exterior of calibration frame 36 may improve accuracy over a system where fiducials are mounted away from the area where surgery is being performed. Without wishing to be bound by theory, simulation, and/or modeling, it is believed that a reason for improved accuracy is that optimal accuracy of tracking markers 8 may be achieved if tracking markers 8 are placed around the perimeter of calibration frame 36 being tracked.

Figure 4E:
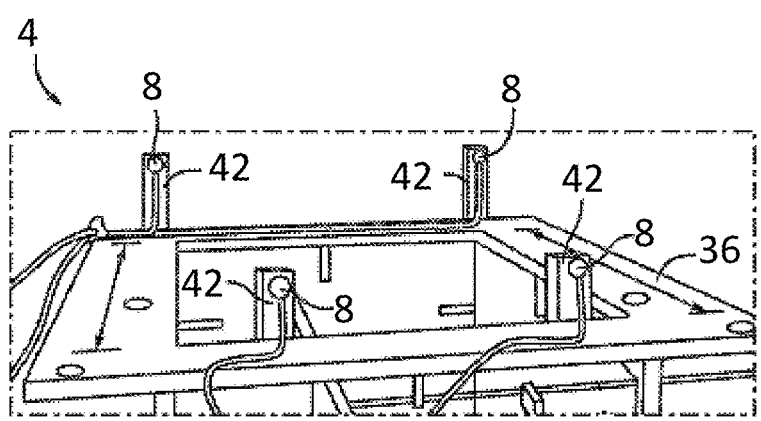
FIG. 4E illustrates an embodiment of the use of calibration frames with the guidance system.

Further embodiments of calibration frame 36 are illustrated in FIG. 4E. This embodiment is simplified to make it less obstructive to the surgeon. In some embodiments, calibration frame 36 may comprise four tracking markers 8 having a lower profile than tracking markers 8 described above and depicted in FIGS. 4A-4D. For example, calibration frame 36 may comprise a plurality of upright posts 42 that are angled away from calibration frame 36 by about 10°. In some embodiments, tracking markers 8 are mounted on posts 42 that are angled back by 10°, and this angulation keeps tracking markers 8 facing toward the cameras despite the patient being horizontal.

Moreover, in some embodiments, a pair of the tracking markers 8 positioned on the front of calibration frame 36 may be configured to have less chance of obscuring the pair of tracking markers 8 positioned on the rear of calibration frame 36. For example, posts 42 that are farthest away from the camera or farthest from a detection device of a tracking system 44, as illustrated in FIGS. 9A, 9B, 10A, and 10B, may be taller and spaced farther laterally than posts 42 closest to the camera.

In additional embodiments, calibration frame 36 may comprise fiducial markers 24 that comprise radio-opaque properties for detection by a medical imaging scanner, and tracking marker 8 properties, allowing fiducial markers 24 to be visible by cameras or otherwise detectable by real-time tracking system 44. In some embodiments, relationship between fiducial marker 24 and tracking markers 8 may not need to be measured or established because fiducial marker 24 contains properties of both types of detection. Therefore, in some embodiments, as soon as the position is determined from the CT scan (or other imaging scan), the spatial relationship between robot 46 and anatomy of patient 1 may be defined.

In other embodiments, DRA 4 may comprise a flexible roll configuration. In some embodiments, DRA 4 may comprise three or more radio-opaque fiducial markers 24 that define a rigid outer frame and nine or more tracking markers 8 embedded in a flexible roll of material. As described earlier, fiducial markers 24 may be visible on CT scans and/or other medical diagnostic images, such as MRI, or reconstructions from O-arm or Iso-C scans, and their centroids may be determined from the 3D image. Tracking markers 8 may include tracking markers 8 that have 3D coordinates that are detectable in real-time using cameras or other means. Some embodiments may utilize tracking marker systems based on reflective optical systems, infrared-emitting marker systems, electromagnetic systems, or a Local Positioning System ("LPS").

In some embodiments, DRA 4 may be an adherable fixture, configured for temporary attachment to the skin of a patient 1. For example, in some embodiments, DRA 4 may be temporarily adhered to the patient 1 during imaging, removed, and then subsequently reattached during a follow-up medical procedure, such as a surgery. In some embodiments, DRA 4 may be applied to the skull of a patient 1 for use in placement of electrodes for deep brain stimulation. In some embodiments, this method may use a single scaffold 6, or two related scaffold 6. In this instance, the two related scaffolds 6 may share the same surface shape. However, one scaffold 6 may be temporarily attached at the time of medical image scanning, and may include fiducial markers 24 (but not tracking markers 8), and second scaffold 6 may be attached at the time of surgery, and may include tracking markers 8 (but not fiducial markers 24).

Figure 5A:
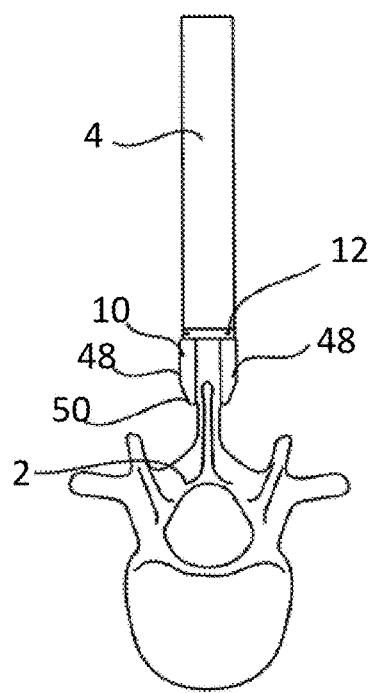
FIG. 5A illustrates an embodiment of an dynamic reference array, comprising a modified mount with a clamping mechanism.
Figure 5B:
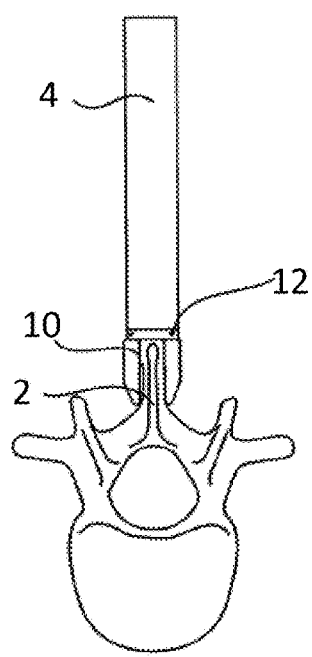
FIG. 5B illustrates an embodiment of an dynamic reference array, comprising a modified mount with a clamping mechanism.
Figure 5C:
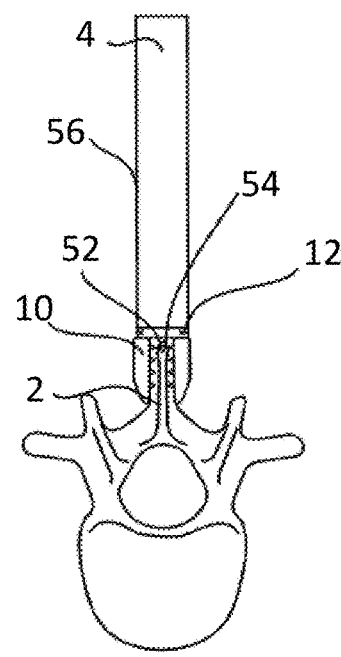
FIG. 5C illustrates an embodiment of an dynamic reference array, comprising a modified mount with a clamping mechanism.

In embodiments of the invention, DRA 4 may comprise a conventional clamping mechanism 10 (e.g., FIG. 1) for securely attaching DRA 4 to patient 1. For example, in some embodiments, DRA 4 may be configured to clamp to spinous process 10 of a patient 1 after the surgeon has surgically exposed spinous process 10. FIGS. 5A-5C shows the lower support of a DRA 4 mounted to spinous process 10 in the lumbar spine of a patient 1 in accordance with some embodiments.

In embodiments, during use of a DRA 4 having a conventional clamping mechanism 10 with image guidance, the relationship between fiducial markers 24 and the bony anatomy of patient 1 may be established using a registration process wherein known landmarks are touched with a digitizing probe at the same time that tracking markers 8 on the tracker are visible. In some embodiments of the invention, the probe itself may have a shaft protruding from a group of fiducial markers 24, or tracking markers 8, thereby permitting tracking system 44, illustrated in FIGS. 9A, 9B, 10A, and 10B, to calculate the coordinates of the probe tip relative to fiducial markers 24, or tracking markers 8.

In embodiments, clamping mechanism 10 of DRA 4 may be configured for clamping to spinous process 10, or may be configured for anchoring to bone of patient 1 such that DRA 4 may be substantially stationary and not easily moved. In some further embodiments, DRA 4 may comprise at least three tracking markers 8 and distinct fiducial markers 24 that are detected on the CT or other 3D image, preferably near clamp 10 (to be close to bone). In embodiments, tracking markers 8 themselves may be configured to be visualized accurately on CT or other 3D image. In certain embodiments, the portion of scaffold 6 containing fiducial markers 24 may be made to be detachable to enable removal from scaffold 6 after the 3D image is obtained. In embodiments, a combination of fiducial markers 24 and tracking markers 8 may allow tracking with robot 46 in the same way that is possible with the frame-type DRA 4 described above.

As a further illustration of a procedure using an alternate guidance system, in some embodiments, the steps of an open screw insertion procedure utilizing an optical guidance system is described. In some embodiments, after surgical exposure, a DRA 4 comprising a small tree of tracking markers 8, for example tracking markers 8, may be attached to a bony prominence in the area of interest. In some embodiments, conventional calibration procedures for image guidance may be utilized to establish the anatomy relative to tracking system 44 and medical images. For another example, DRA 4 may contain rigidly mounted, substantially permanent or detachable fiducial markers 24 that may be imaged with a CT scan. In some embodiments, the calibration procedures consistent with those stated for calibration frame 36 may be utilized to establish the anatomy relative to robot 46 and the medical image.

In embodiments, an extension to the methods for reconstructing tracking markers 8 is to use multiple ambiguous synchronized lines of sight via multiple cameras tracking the same tracking markers 8. For example, two or more cameras may be set up from different perspectives focused on tracking markers 8 on DRA 4 or robot 46. In embodiments, one camera unit may be placed at the foot of a patient's bed, and another may be attached to robot 46. In some embodiments, another camera unit may be mounted to the ceiling. In embodiments, when all cameras substantially simultaneously view tracking markers 8, coordinates may be transformed to a common coordinate system, and the position of any of tracking markers 8 may be considered to be the average (mean) of that marker's three dimensional position from all cameras used. In embodiments, even with extremely accurate cameras, an average may be needed because with system noise, the coordinates as perceived from different cameras may not be exactly equal. However, when one line of sight is obscured, the lines of sight from other cameras (where tracking markers 8 may still be viewed) may be used to track robot 46 and DRA 4. In embodiments, to mitigate twitching movements of robot 46 when one line of sight is lost, it is possible that tracking marker 8 positions from the obscured line of sight may be reconstructed using methods as previously described based on an assumed fixed relationship between the last stored positions of tracking markers 8 relative to the unobstructed lines of sight. Further, in embodiments, the position of tracking marker 8 from camera one relative to its position from camera two may be stored; then if camera one is obstructed, and until the line of sight is restored, this relative position may be recalled from computer memory (for example in memory of a computer platform) and a reconstruction of tracking marker 8 from camera one may be inserted based on the recorded position of tracking marker 8 from camera two. In some embodiments, the method may compensate for temporary obstructions of line of sight such as a person standing or walking in front of one camera unit.

In embodiments, instead of a DRA 4 consisting of a combination of fiducial markers 24 and tracking markers 8, it is possible to register a primary DRA 4 through an intermediate registration of another temporary DRA 4. For example, in some embodiments, an example of such a calibration method may include attaching a temporary rigid plate, not illustrated, that contains fiducial markers 24, open mounts (such as snaps, magnets, Velcro, or other features) to which tracking markers 8 may at any time be attached in a known position. The method may then include scanning the subject (using for example CT, MRI, etc.), followed by attaching a primary DRA 4, not illustrated, such as those described earlier or other DRA with three or more tracking markers 8 rigidly affixed to the anatomy of a patient 1, and then attaching tracking markers 8 to the temporary DRA 4 in the known positions dictated by the snaps, magnets, velcro, etc. This primary DRA 4 may not require any fiducial markers 24 because registration is performed through the temporary DRA's 15 fiducial marker 24 positions. In some embodiments, a further step may include activating cameras to read the position of the primary DRA 4 affixed to the anatomy of patient 1 at the same time as second temporary DRA 4. This step establishes the position of tracking markers 8 on the temporary DRA 4 relative to the positions of tracking markers 8 on the primary DRA 4, because the position of fiducial markers 24 on the temporary DRA 4 are known relative to tracking markers 8 on the temporary DRA 4, establishing the position of the anatomy relative to tracking markers 8 on the primary DRA 4. After establishing position, the temporary DRA 4 may be removed, including its tracking markers 8 and fiducial markers 24. These markers are no longer needed because registration has been transferred to the tracking markers 8 on the rigidly affixed primary DRA 4.

Figure 6A:
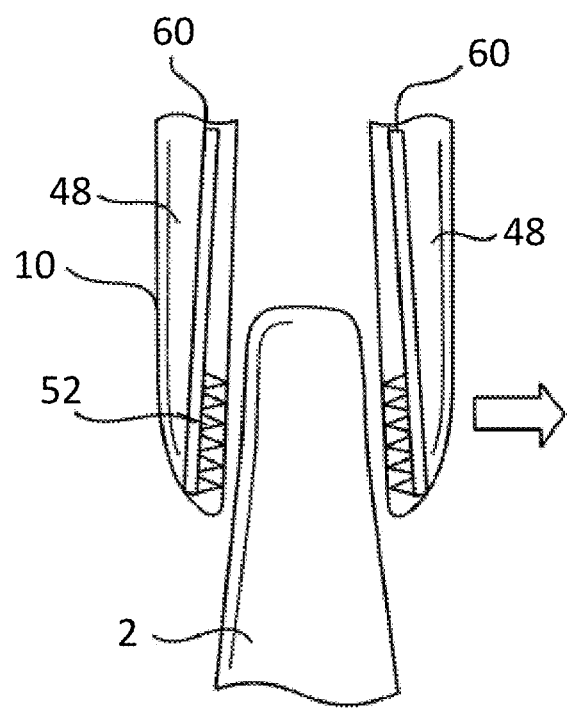
FIG. 6A illustrate an embodiment of clamping mechanism actuation on a spinous process.
Figure 6B:
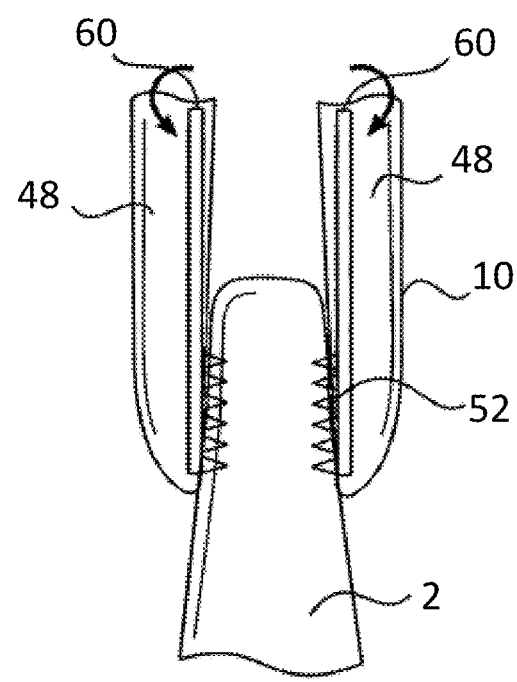
FIG. 6B illustrate an embodiment of clamping mechanism actuation on a spinous process.

In embodiments, as illustrated in FIGS. 5A-5C, may comprise a modification to DRA 4 allowing DRA 4 to slide a clamping mechanism 10 over spinous process 2 without full exposure of spinous process 240. As illustrated, clamping mechanism 10 may comprise clamps 48 including at least one beveled edge 50, and clamp teeth 52. During an operation, a surgeon may make a stab incision in the midline and then slide clamps 48 of clamping mechanism 10 down along the sides of spinous process 2, pushing tissue away as the tip of clamping mechanism 10 is advanced. In some embodiments, as illustrated in FIGS. 6A and 6B, the leading edge of clamping mechanism 10 may be beveled (see leading beveled edges 50 of each clamp 48 of clamping mechanism 10), and have a shape similar to a periosteal elevator. This shape may allow clamping mechanism 10 to separate the muscle tissue from the bony spinous process 2 as it is advanced. In some embodiments, leading beveled edges 50 of clamping mechanism 10 may be electrified to enable it to more easily slide through muscle and connective tissues to prevent excessive bleeding.

In some embodiments, a mechanism activated from farther back on the shaft (for example a turn screw, or conventional spring, etc.) may be activated to deploy clamp teeth 52 on clamps 48. The same mechanism or another mechanism may close and compress clamps 48 together to firmly secure clamping mechanism 10 to spinous process 2 (see FIGS. 5B-5C). Additionally, in some embodiments, a screw 54 aligned with a handle 56 may deploy by threading into spinous process 2 (see for example, FIG. 5C).

The embodiments as described above and illustrated in FIGS. 5A-5C may be especially well suited to percutaneous pedicle screw-rod surgery because the hole made for mounting clamping mechanism 10 may also be used as the hole for inserting the conventional rod to interconnect the conventional pedicle screw heads. Further, the embodiments as described above and illustrated in FIGS. 5A-5C may also be useful for mounting a marker tree (for other bony prominences, such as transverse processes, long bones, skull base, or others).

FIGS. 6A-6B and 7A-7B illustrate embodiments of clamping mechanism 10 actuation on a spinous process 2 in accordance with some embodiments. In some embodiments, the mechanism for deploying clamp teeth 52 may be comprise a hollow cavity 58 containing clamp teeth 52 that are to one side of hollow cavity 58 during insertion, but may be forced toward the opposite side when the mechanism is deployed, such that the embedded teeth penetrate the bone (see the illustration of penetrated clamp teeth 52 in FIGS. 7A and 7B).

Figure 7A:
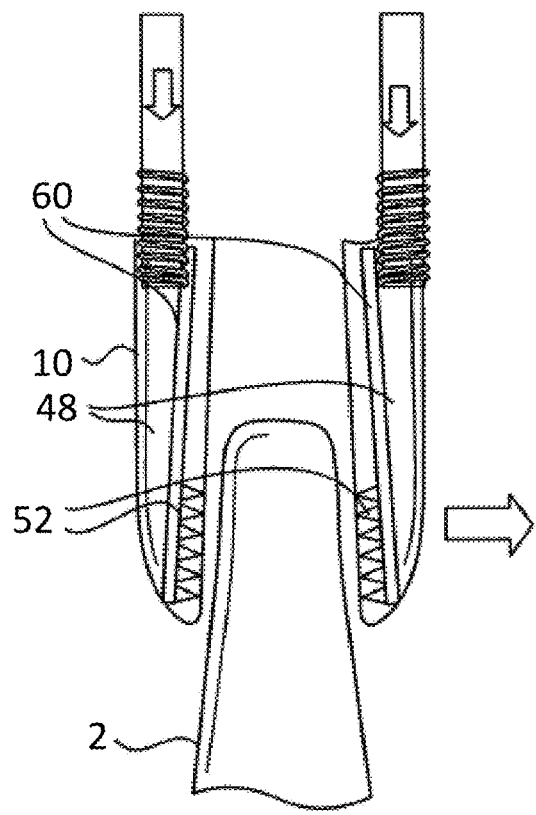
FIG. 7A illustrate an embodiment of clamping mechanism actuation on a spinous process.
Figure 7B:
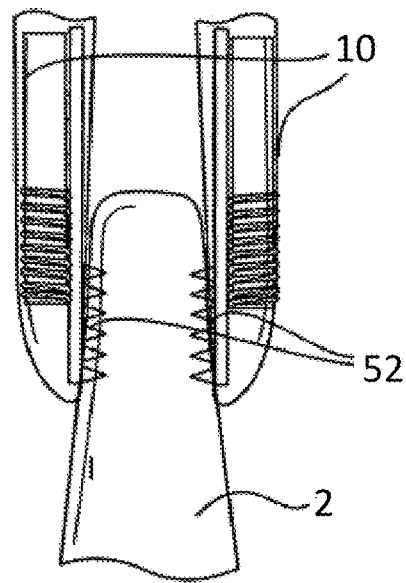
FIG. 7B illustrate an embodiment of clamping mechanism actuation on a spinous process.

FIGS. 7A-7B illustrate an alternative embodiment of clamping mechanism 10 actuation on a spinous process 2. As illustrated, the groups of clamp teeth 52 may be attached to rods 60 that run down hollow cavity 58. Rods 60 may pivot farther up handle 56 (pivot point not pictured) and force clamp teeth 52 together. For example, in embodiments, rods 60 may be driven into hollow cavity 58 on the side away from the bone, forcing clamp teeth 52 against and into the bone (for example, see the penetrated clamp teeth 52 in FIG. 7B).

As described above, fiducial markers 24 may be present in a CT scan of the anatomy. However, it may be desirable to crop CT scans as close as possible to the spine to improve resolution. In some embodiments, instead of using fiducial markers 24 near where tracking markers 8 are located, an alternative may be to have a rigid extension containing fiducial markers 24 that may be temporarily attached near spinal process 2 when the scan is taken. In some embodiments, clamping mechanism 10 may be coupled with, or otherwise modified with a DRA 4. For example, FIGS. 8A-8B illustrate a clamping mechanism 10 modified with a DRA 4 including a temporary marker skirt 62 in accordance with at least one embodiment of the disclosure, and FIG. 8B illustrates a clamping mechanism 10 modified with a DRA 4 as illustrated in FIG. 8A with temporary marker skirt 62 detached in accordance with at least one embodiment of the disclosure. As illustrated, temporary marker skirt 62 may include fiducial markers 24 in a temporary "skirt" around the base of clamping device 10. The design of temporary marker skirt 62 and clamping device 10 may be such that fiducial markers 24 in skirt 62 have known locations relative to tracking markers 8 for tracking that are farther away. Once the scan is taken, fiducial markers 24 may not be needed. Therefore, in embodiments, by depressing a conventional release, temporary marker skirt 62 may be removed, so it will not be in the way of the surgeon (see for example FIG. 8B).

Figures 9A, 9B:
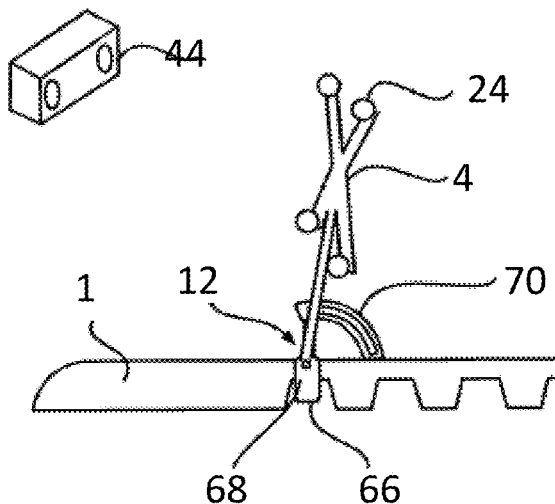
FIG. 9A illustrates a dynamic reference array in a lowered position.
FIG. 9B illustrates a dynamic reference array in a upper position

In embodiments, as illustrated in FIGS. 9A-9B, a DRA 4 may have a swiveling feature 12 that enables the position of some or all tracking markers to be shifted after the scan is captured. One benefit of this feature is that it allows the radio-opaque markers to be positioned in the location that is most appropriate for the CT scan—near the anatomy, close to the skin, as illustrated in FIG. 9A. For example, the DRA 4 may be positioned generally flat (e.g., angled about 10° or less) along the patient. Then after the CT scan, it allows the user to swing the DRA 4 upwards, placing fiducial markers 24 away from surgery, while simultaneously positioning the tracking markers in a position that is appropriate for tracking, as illustrated in FIG. 9B. For example, the DRA 4 may be moved into an upright position. Swiveling may enable fiducial markers 24 to be mounted nearer to the tracking markers than other designs, thereby making the entire DRA 4 more compact. Swiveling may allow the same markers to double as both radio-opaque fiducial markers 24 and tracking markers 8. For example, reflective tracking spheres may be manufactured with a metal or ceramic core that is radio-opaque.

Figure 10A:
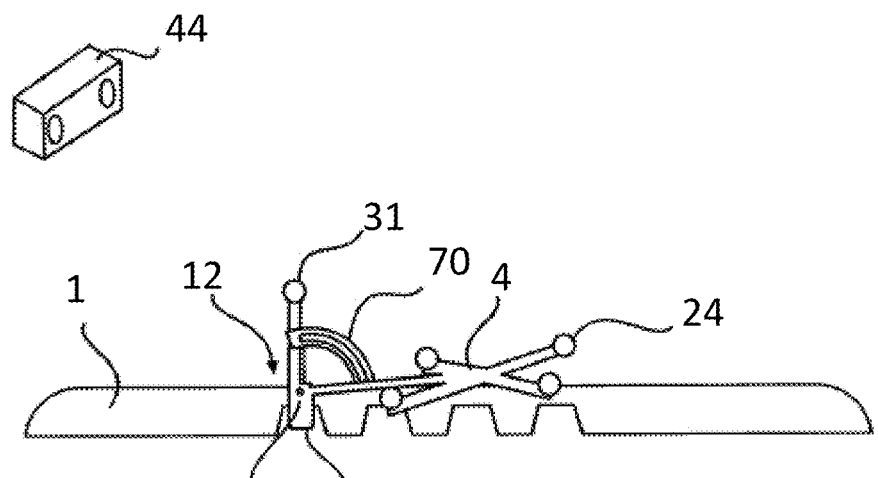
FIG. 10A illustrates a dynamic reference array in a lowered position with an alternate tracker in a static position.
Figure 10B:
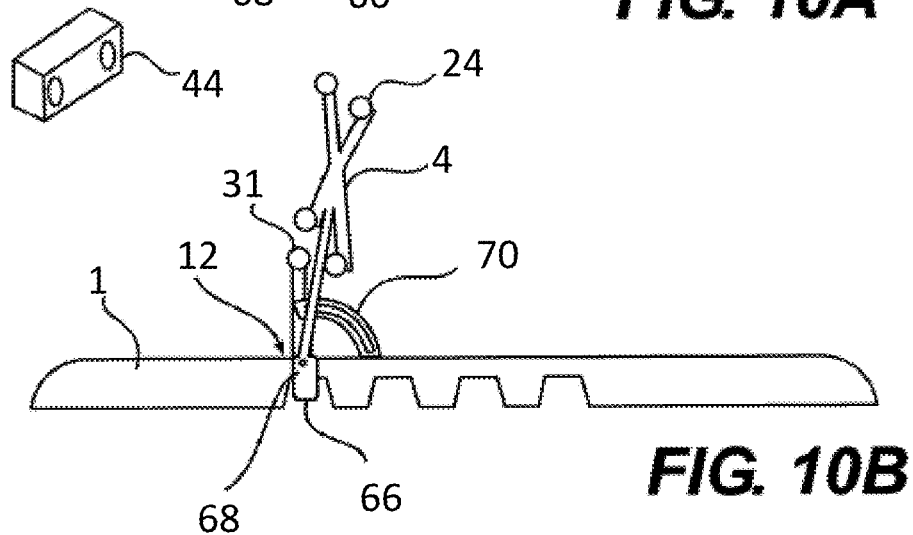
FIG. 10B illustrates a dynamic reference array in a lowered position with an alternate tracker in an static position.

An additional benefit and feature of the swiveling feature 12 may be that one or more of fiducial markers 24, or tracking markers 8, may be made to move relative to the other tracking markers during swiveling, altering the rigid body relationship of the tracking markers, as illustrated in FIG. 10A-10B. In other words, the relative positioning of one or more of fiducial markers 24, or tracking markers 8, may shift relative to the configuration that is stored in computer memory and compared during any given tracking frame. When the rigid body array spacing is altered, it is possible for software to determine whether the array is down or up automatically. This feature prevents the user from inadvertently trying to track and navigate before DRA 4 is swiveled into the correct position. Additionally, one or more fiducial markers 24 may be made to move relative to other fiducial markers 24 during swiveling, meaning two discrete rigid body arrangements may be observed on the CT scan, allowing software to automatically detect whether the array was up or down during the scan. This may prevent the user from inadvertently trying to track and navigate before DRA 4 is in the correct position. FIGS. 10A-10B illustrates a configuration where one fiducial marker 24, or tracking marker 31, may not swivel with a plurality of additional fiducial markers 24, and/or tracking markers 8.

To properly swivel, DRA 4 may comprise a base 66 which may be part of the clamping mechanism 10. Base 66 may be attached at a connection point 68 to DRA 4, with fiducial markers 24 and/or tracking markers 8, by any suitable means. Suitable means may be, but is not limited to a ball joint, a hinge, a slide, or any combination thereof. Furthermore, DRA 4 may swivel in any direction in relation to base 66. This may allow the structure to move from side to side, up or down, diagonally, or any combination thereof. Movement of DRA 4 in relation to base 66 may further be aided by a guide 70 or external member. In embodiments, not illustrated, a DRA 4 may swivel at more than one location located on base 66 or DRA 4.

Figure 11A:
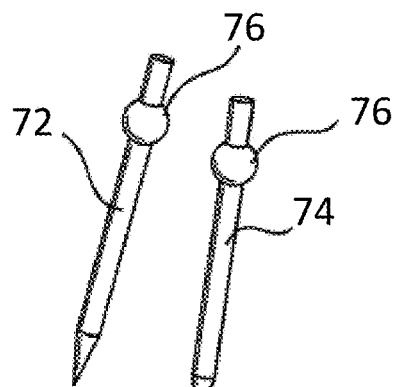
FIG. 11A illustrates two posts that may be used to anchor the dynamic reference array to bone.
Figure 11B:
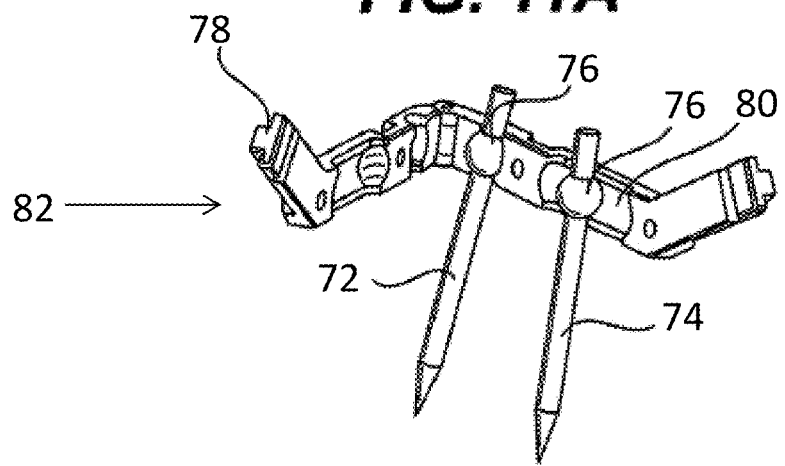
FIG. 11B illustrates an interior view of an open clamp used to secure the two posts in a selected position.
Figure 11C:
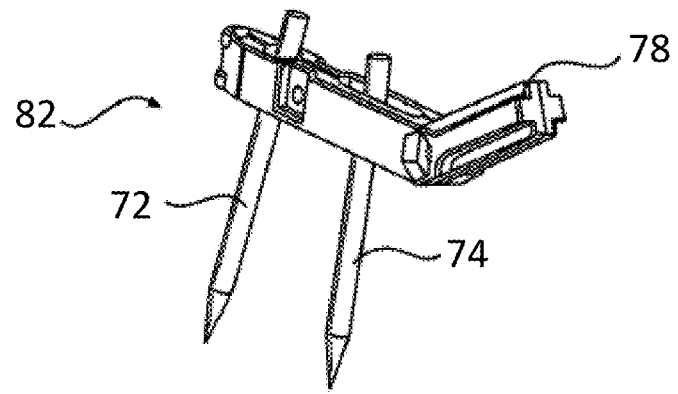
FIG. 11C illustrates a closed clamp, securing the two posts from movement.

In some cases, it may not be possible to mount a clamp mechanism 10. For example, surgery may be intended on a region other than the spine, or surgery may be intended in cases in which the patient previously had the spinous process removed. As illustrated in FIGS. 11A-11C, an alternate method for mounting a DRA 4 rigidly to the bone of patient 1 may consist of two posts 72 and 74 onto which a DRA 4 clamps. It is contemplated that two posts 72 and 74 may have a spherical feature 76 to constrain some translational and rotational degrees of freedom, enabling locking of DRA 4 in a rigidly fixed and repeatable position by clamp 78. Clamp 78, in embodiments, may serve as a base in which swivel feature 12 may seat. For this two-post method, as illustrated in FIGS. 11A-11C, the interior of clamp 78 secured to a post 72 may have a socket-shaped feature with a flared through-hole. Clamp 78 may constrain all translation of the socket piece while still allowing it to rotate. Part of DRA clamp 78 around post 76 may have an elongated socket 80 with a racetrack shaped through-hole. This feature may constrain all rotation of DRA 4 and translation of the other pin in most directions. This configuration may allow two-post DRA 82 to be clamped into a unique orientation and position then removed and repeatedly re-attached to the same position.

In an embodiment, where mounting post 72 to a different vertebra than post 74, this configuration does not prevent translation of post 72 toward or away from post 74, in which case post 74 may slide inside elongated socket 80. It may be possible to tighten tolerances so that when two-post DRA 82 is clamped around post 74, friction disallows such translation. Or such shifting may be monitored through surveillance markers.

Although the present invention and its advantages have been described in detail, it should be understood that various changes, substitutions and alterations may be made herein without departing from the spirit and scope of the invention as defined by the appended claims.

What is claimed is:

1. A dynamic reference array, comprising:
a scaffold;
a plurality of tracking markers trackable by a camera;
a plurality of fiducial markers, separate from the plurality of tracking markers, coupled to the scaffold, wherein the plurality of fiducial markers are detected in a medical image associated with a patient; and
an attachment structure coupled to the scaffold with a swivel feature, wherein the attachment structure is configured to secure the scaffold to the patient while allowing movement of the scaffold with respect to the attachment structure,
wherein in a first position, the attachment structure is configured to position the plurality of fiducial markers near a surface of the patient and in a second position, the attachment structure is configured to position the plurality of fiducial markers away from the surface of the patient, and
wherein at least one of the plurality of tracking markers is disposed on a post of the attachment structure and remains stationary with respect to the swivel mechanism, and
an image guidance software configured to automatically determine whether the tracking or fiducial markers are in the first or second position for purposes of preventing inadvertent tracking and navigation by comparing the position of one of the at least one of the stationary tracking markers with the position of one of the at least one of the plurality of fiducial markers positioned on the attachment structure when the attachment structure is in the first position and comparing the position of the one of the at least one of the stationary tracking markers with the position of the one of the at least one of the plurality of fiducial markers positioned on the attachment structure when the attachment structure is in the second position.

2. The dynamic reference array of claim 1, wherein the plurality of tracking markers are infrared markers and the plurality of fiducial markers are radio-opaque markers.

3. The dynamic reference array of claim 1, wherein the attachment structure is a ball joint, a hinge pin, or a slide mechanism.

4. The dynamic reference array of claim 1, wherein the attachment structure comprises a clamp with a hinge pin.

5. The dynamic reference array of claim 1, wherein the attachment structure comprises a clamp.

6. A dynamic reference array, comprising:
a scaffold;
a plurality of first markers coupled to the scaffold, wherein the plurality of first markers are trackable by a camera and configured to be detected in a medical image associated with a patient,
an attachment structure coupled to the scaffold with a swivel feature, wherein the attachment structure is configured to secure the scaffold to the patient while allowing movement of the scaffold with respect to the attachment structure,
wherein the plurality of first markers contain a metallic or ceramic core that is radio-opaque,
wherein in a first position, the attachment structure is configured to position the plurality of first markers near a surface of the patient and in a second position, the attachment structure is configured to position the plurality of first markers away from the surface of the patient, and
wherein a second marker trackable by the camera is disposed on a post of the attachment mechanism and remains stationary with respect to the swivel feature,
an image guidance software configured to automatically determine whether the tracking or fiducial markers are in the first or second position for purposes of preventing inadvertent tracking and navigation by comparing the position of one of the at least one of the stationary tracking markers with the position of one of the at least one of the plurality of fiducial markers positioned on the attachment structure when the attachment structure is in the first position and comparing the position of the one of the at least one of the stationary tracking markers with the position of the one of the at least one of the plurality of fiducial markers positioned on the attachment structure when the attachment structure is in the second position.

* * * * *